(12) United States Patent
Miller (10) Patent No.: US 8,097,740 B2
(45) Date of Patent: Jan. 17, 2012

(54) ISOLATION AND SUBSEQUENT UTILIZATION OF SATURATED FATTY ACIDS AND α-OLEFINS IN THE PRODUCTION OF ESTER-BASED BIOLUBRICANTS

(75) Inventor: Stephen Joseph Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 650 days.

(21) Appl. No.: 12/122,894

(22) Filed: May 19, 2008

(65) Prior Publication Data
US 2009/0285728 A1    Nov. 19, 2009

(51) Int. Cl.
*C07C 51/00*    (2006.01)
(52) U.S. Cl. ........................... 554/148; 560/176
(58) Field of Classification Search .............. 554/148, 554/149; 560/176
See application file for complete search history.

(56) References Cited

U.S. PATENT DOCUMENTS

| | | | | |
|---|---|---|---|---|
| 3,317,465 A | * | 5/1967 | Doyle et al. | 528/89 |
| 3,327,014 A | * | 6/1967 | Noddings | 585/667 |
| 3,489,775 A | * | 1/1970 | Menguy et al. | 549/529 |
| 4,017,429 A | | 4/1977 | Steele et al. | |
| 5,936,107 A | | 8/1999 | Raths | |
| 6,150,458 A | * | 11/2000 | Weikard et al. | 525/31 |
| 6,150,577 A | | 11/2000 | Miller et al. | |
| 6,281,404 B1 | | 8/2001 | Miller | |
| 6,822,126 B2 | | 11/2004 | Miller | |

FOREIGN PATENT DOCUMENTS
EP    1529828    5/2005
WO    WO98/21170    5/1998

OTHER PUBLICATIONS

U.S. Appl. No. 11/673,879, filed Feb. 12, 2007, Miller, et al.
U.S. Appl. No. 12/023,695, filed Jan. 31, 2008, Miller, et al.
H. Schulz, "Short history and present trends of Fischer-Tropsch synthesis," Applied Catalysis A, vol. 186, pp. 3-12 (1999).
M. Schroder, Chem. Rev. vol. 80, p. 187, 1980.

* cited by examiner

*Primary Examiner* — Deborah D Carr
(74) *Attorney, Agent, or Firm* — Peter L. Prater; Edward Mickelson (57) ABSTRACT

The present invention is generally directed to the synthesis and/or manufacture of ester-based lubricant compositions. The present invention is also directed to methods of making these and other similar lubricant compositions, and to systems for implementing such methods (processes). In some embodiments, the methods for making such ester-based lubricants utilize a biomass precursor (e.g., triglyceride-bearing vegetable oils) such that the lubricant compositions generated by the methods and systems of the present invention can be properly deemed biolubricants. In these or other embodiments, lubricant precursor species can also be sourced or derived from Fischer-Tropsch (FT) and/or long-chain paraffin pyrolysis reaction products. The ester component of the lubricant compositions, produced in accordance with the methods and systems of the present invention, comprises largely diester species.

10 Claims, 7 Drawing Sheets

Scheme 1

Octanoic acid 2-octanoyloxy-dodecyl ester (8)

ISOLATION AND SUBSEQUENT UTILIZATION OF SATURATED FATTY ACIDS AND α-OLEFINS IN THE PRODUCTION OF ESTER-BASED BIOLUBRICANTS

FIELD OF THE INVENTION

This invention relates to the formation of ester-based lubricants—particularly wherein they are at least partially-derived from at least one biologically-derived precursor, and wherein at least one olefinic precursor species is generated by Fischer-Tropsch synthesis and/or pyrolysis of long-chain paraffinic species.

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In full synthetic motor oils, however, esters are almost always used in combination with PAOs to balance the effect on seals, solubility of additives, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than traditional lubricants and tend to have much higher flash points and much lower vapor pressures. Ester lubricants are excellent solvents and dispersants, and they can readily solvate and disperse the degradation by-products of oils. Therefore, they greatly reduce sludge buildup. While ester lubricants are stable to thermal and oxidative processes, the ester functionalities give microbes a handle to do their biodegrading more efficiently and more effectively than their mineral oil-based analogues. However, the preparation of esters is more involved and more costly than the preparation of their PAO counterparts.

In view of the foregoing, a simpler, more efficient method of generating ester-based would be extremely useful—particularly wherein such methods utilize renewable raw materials in combination with converting low value olefins (e.g., those that are Fischer-Tropsch derived) to high value ester lubricants.

BRIEF DESCRIPTION OF THE INVENTION

The present invention is generally directed to the synthesis and/or manufacture of ester-based (e.g., comprising diesters) lubricant compositions. The present invention is also directed to methods of making these and other similar lubricant compositions, and to systems for implementing such methods (processes). Generally, the methods for making such ester-based lubricants utilize (at least partly) a biomass (e.g., triglyceride-containing) precursor. In these or other embodiments, lubricant precursor species can also be sourced or derived from Fischer-Tropsch (FT) and/or pyrolysis of long-chain paraffinic species reaction products.

In some embodiments, the present invention is directed to processes comprising the steps of (a) generating and subsequently isolating α-olefins from a process selected from the group consisting of Fischer-Tropsch processing of syngas, pyrolysis of long-chain paraffinic species (e.g., polyethylene and/or FT wax), and combinations thereof; (b) isomerizing the α-olefins to form internal olefins; (c) epoxidizing the internal olefins to form epoxides comprising an epoxide ring; and (d) esterifying the epoxides with a quantity of carboxylic acid to form ester species, wherein the carboxylic acid is derived via the following substeps: (i) hydrolyzing a triglyceride-bearing vegetable oil so as to generate a mixture of free fatty acids of varying degrees of saturation; and (ii) subjecting the mixture of free fatty acids to a separation technique to substantially isolate saturated fatty acids contained therein for use in esterifying the aforementioned epoxides. In some such process embodiments, the step of esterifying proceeds through a diol intermediate. In some or other such embodiments, the step of esterifying proceeds via a direct esterification of the epoxides. Typically, ester products formed by such processes are mixed with other species to form ester-based lubricants.

In some or other embodiments, the present invention is directed to one or more systems for producing ester-based biolubricants, such systems comprising: (a) one or more reactor units for generating and subsequently isolating α-olefins via a technique selected from the group consisting of Fischer-Tropsch processing of syngas, pyrolysis of long-chain paraffinic species, and combinations thereof; (b) an isomerization unit for catalytically-isomerizing the α-olefins to form internal olefins; (c) an epoxidation reactor for converting at least some of the internalized olefins to epoxides; and (d) an esterification unit for esterifying the epoxides with carboxylic acids to form ester species, wherein the carboxylic acids are derived from vegetable oil via a subsystem comprising: (i) a hydrolysis unit for hydrolyzing the triglyceride-bearing vegetable oil so as to generate a mixture of free fatty acids of varying degrees of saturation; and (ii) a separation unit for separating the mixture of free fatty acids so as to substantially isolate saturated fatty acids contained therein for use in esterifying the aforementioned epoxides. In some such embodiments, the esterification unit permits the esterification of the epoxides to proceed directly, whereas in some or other embodiments, the esterification unit permits the esterification of the epoxides to proceed through diol intermediates. In some such embodiments, the one or more reactor units additionally generate transportation fuel.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. Introduction

As mentioned in a preceding section, the present invention is generally directed to the synthesis and/or manufacture of ester-based lubricant compositions. The present invention is also directed to methods of making these and other similar lubricant compositions, and to systems for implementing such methods (i.e., processes). In some embodiments, the methods for making such ester-based lubricants utilize a biomass precursor (e.g., triglyceride-bearing vegetable oils) such that the lubricant compositions generated by the methods and systems of the present invention can be properly deemed "biolubricants." In these or other embodiments, lubricant precursor species can also be sourced or derived from Fischer-Tropsch (FT) reaction products. The ester component of the lubricant compositions, produced in accordance with the methods and systems of the present invention, comprises largely diester species.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Long-chain paraffinic species," as defined herein, are paraffinic (i.e., alkane) species having 50. or more carbon atoms. Examples of such species include, but are not limited to, polyethylene (e.g., from waste plastic) and FT wax.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g., ASTM Standard Guide and Test Methods D 2270-04, D 445-06, D 6074, and D 2983.

With respect to describing molecules and/or molecular fragments herein, "$R_n$," where "n" is an index, refers to a hydrocarbon group, wherein the molecules and/or molecular fragments can be linear and/or branched.

As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such a resource generally being exclusive of fossil fuels.

The term "internal olefin," as used herein, refers to an olefin (i.e., an alkene) having a non-terminal carbon-carbon double bond (C=C). This is in contrast to "α-olefins" which do bear a terminal carbon-carbon double bond.

3. Diester Lubricant Compositions

The lubricant compositions produced by the methods and systems of the present invention are described in commonly-assigned U.S. patent application Ser. No. 11/673,879; filed Feb. 12, 2007; and Ser. No. 12/023,695; filed Jan. 31, 2008. Generally, the ester-based lubricant compositions described herein comprise a quantity of diester species having the following chemical structure:

where $R_1$, $R_2$, $R_3$, and $R_4$ are the same or independently selected from a $C_2$ to $C_{17}$ carbon fragment.

Regarding the above-mentioned diester species, selection of $R_1$, $R_2$, $R_3$, and $R_4$ can follow any or all of several criteria. For example, in some embodiments, $R_1$, $R_2$, $R_3$, and $R_4$ are selected such that the kinematic viscosity of the composition at a temperature of 100° C. is typically 3 centistokes (cSt) or greater. In some or other embodiments, $R_1$, $R_2$, $R_3$, and $R_4$ are selected such that the pour point of the resulting lubricant is −20° C. or lower. In some embodiments, $R_1$ and $R_2$ are selected to have a combined carbon number (i.e., total number of carbon atoms) of from 6 to 14. In these or other embodiments, $R_3$ and $R_4$ are selected to have a combined carbon number of from 10 to 34. Depending on the embodiment, such resulting diester species can have a molecular mass between 340 atomic mass units (a.m.u.) and 780 a.m.u.

Figure 1:
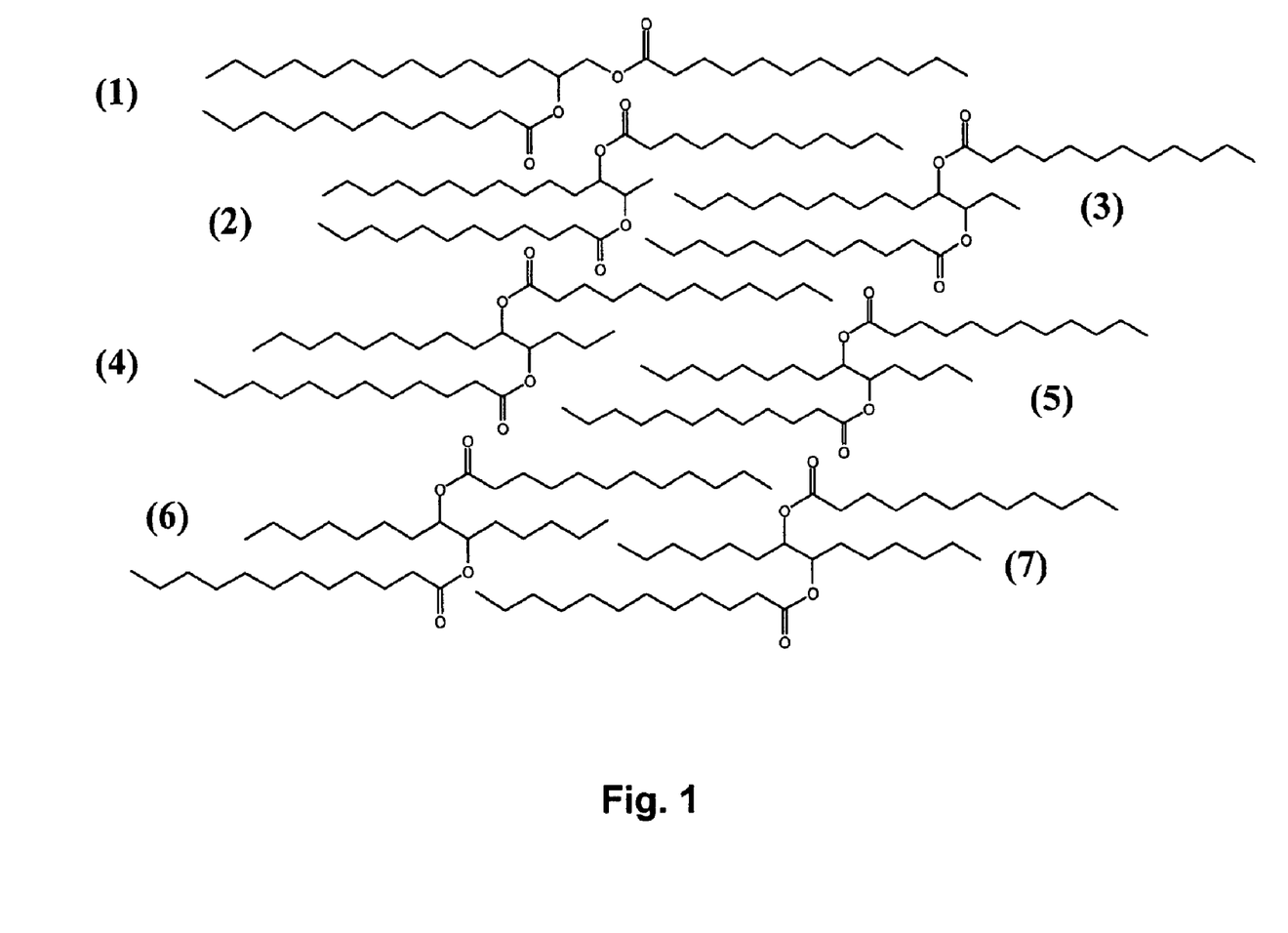
FIG. 1 depicts diester compounds 1-7, such compounds being examples of the types of diester species (and compositions thereof) that can be produced in accordance with at least some method and system embodiments of the present invention.

FIG. 1 depicts diester compounds 1-7, such compounds being exemplary diester species of the type described above and, by extension, of the type produced by methods and systems of the present invention—at least in some such method and system embodiments.

In some embodiments, such above-described compositions are substantially homogeneous in terms of their diester component. In some or other embodiments, the diester component of such compositions comprises a variety (i.e., a mixture) of diester and/or monoester species.

In some embodiments, the diester-based lubricant composition further comprises a base oil selected from the group consisting of Group I oils, Group II oils, Group III oils, and mixtures thereof.

It is worth noting that in most applications, the above-described esters and their compositions are unlikely to be used as lubricants by themselves, but are usually used as blending stocks. As such, esters with higher pour points may also be used as blending stocks with other lubricant oils since they are very soluble in hydrocarbons and hydrocarbon-based oils.

4. Methods of Making Ester-Based Lubricants

4.1 General

As mentioned above, in some embodiments the present invention is directed to methods of making the above-described lubricant compositions.

Figure 2:
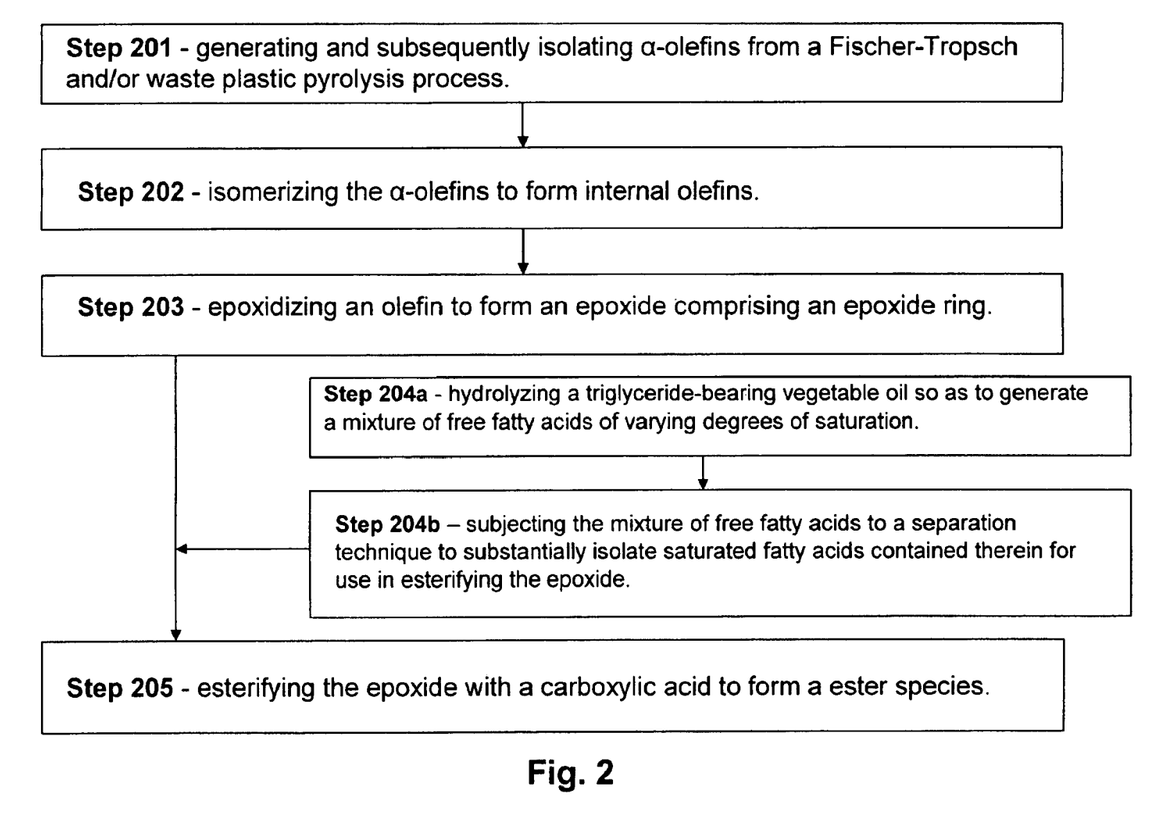
FIG. 2 is a flow diagram illustrating a method of making diester-based lubricant compositions, in accordance with some embodiments of the present invention.

Referring to the flow diagram shown in FIG. 2, in some embodiments the present invention is directed to one or more methods comprising the steps of: (Step 201) generating and subsequently isolating α-olefins from a process such as Fischer-Tropsch (FT) processing of syngas and/or pyrolysis of long-chain paraffinic species; (Step 202) isomerizing the α-olefins to form internal olefins; (Step 203) epoxidizing the internal olefins to form epoxides comprising an epoxide ring; and (Step 205) esterifying the epoxides with a quantity of carboxylic acid to form ester species, wherein the carboxylic acid is derived via the following substeps: (Sub-step 204a) hydrolyzing a triglyceride-bearing vegetable oil so as to generate a mixture of free fatty acids of varying degrees of saturation; and (Sub-step 204b) subjecting the mixture of free fatty acids to a separation technique to substantially isolate saturated fatty acids contained therein for use in esterifying the aforementioned epoxides.

Typically, the α-olefins utilized in the above-described embodiments are olefins in the $C_2$ to $C_{20}$ range. Such α-olefins can comprise a mixture of molecules of varying chain length (heterogeneous mixture), or they can be substantially uniform in length (homogeneous mixture). Commercial and/or processing determinants of the olefin characteristics/properties include, but are not limited to, FT processing and/or long-chain paraffinic species pyrolysis conditions, number and type of a plurality of feeds, and any separation performed subsequent to the processing.

Fischer-Tropsch synthesis of hydrocarbons, and α-olefins in particular, is well established in the art. See, e.g., H. Schulz, "Short history and present trends of Fischer-Tropsch synthesis," Applied Catalysis A, vol. 186, pp. 3-12 (1999). When utilizing FT-derived α-olefins, such olefins can be the primary synthesis product, or merely a by-product, of the associated FT processing.

In some embodiments, wherein the α-olefins are derived (at least in part) from the pyrolysis of long-chain paraffinic species, the pyrolysis is carried out in a manner such as, or in keeping with the spirit of, that/those described in, e.g., U.S. Pat. No. 6,150,577 (Miller et al.) and U.S. Pat. No. 6,822,126 (Miller).

It is often necessary to isomerize the α-olefin so as to internalize the double bond. It is typically necessary to convert alpha olefins to internal olefins because diesters of alpha olefins, especially short chain alpha olefins, tend to be solids or waxes. "(Double-bond) isomerizing" or "internalizing" alpha olefins followed by transformation to the diester functionalities introduces branching along the chain which reduces the pour point of the intended products. The ester groups with their polar character would further enhance the viscosity of the final product. Adding ester branches following the isomerizing (isomerization) step will tend to increase carbon number and hence viscosity. It can also decrease the associated pour and cloud points. It is typically preferable to have a few longer branches than many short branches, since increased branching tends to lower the viscosity index (VI). Such isomerization is typically carried out catalytically using a catalyst such as, but not limited to, crystalline aluminosilicate and like materials and aluminophosphates. See, e.g., U.S. Pat. No. 6,281,404 (Miller).

Regarding the step of epoxidizing (i.e., the epoxidation step), in some embodiments, the above-described olefin (preferably an internal olefin) can be reacted with a peroxide (e.g., $H_2O_2$) or a peroxy acid (e.g., peroxyacetic acid) to generate an epoxide. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253. Olefins can be efficiently transformed to the corresponding diols by highly selective reagent such as osmium tetra-oxide (M. Schroder, Chem. Rev. vol. 80, p. 187, 1980) and potassium permanganate (Sheldon and Kochi, in *Metal-Catalyzed Oxidation of Organic Compounds*, pp. 162-171 and 294-296, Academic Press, New York, 1981).

4.2 Direct Esterification

Figure 3:
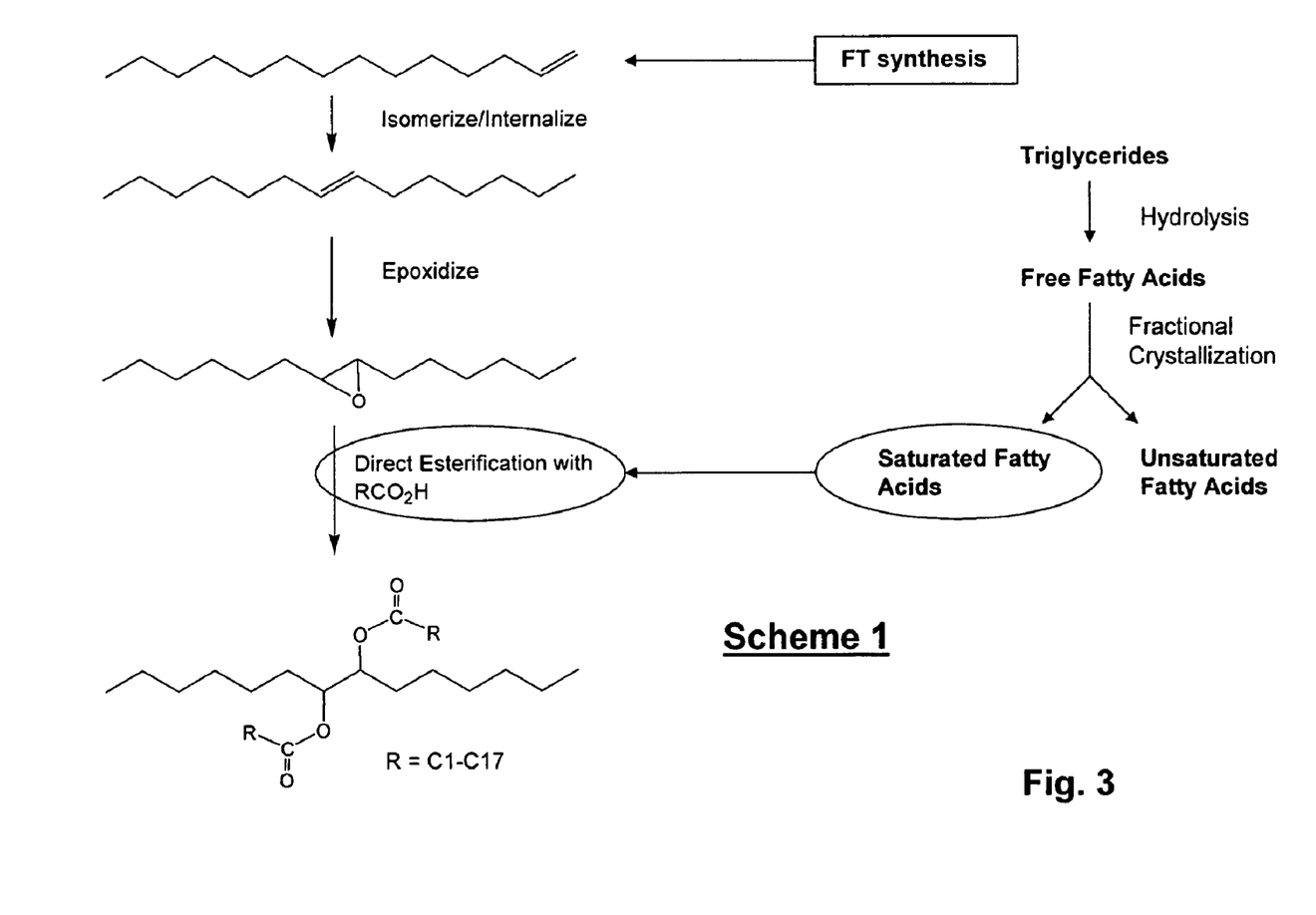
FIG. 3 (Scheme 1) is a chemical flow diagram illustrating an exemplary method of making a diester-based lubricant composition, in accordance with some embodiments of the present invention.

In some embodiments, the step of esterifying proceeds via a direct esterification (with saturated fatty acids) of the epoxide—as shown in FIG. 3, Scheme 1. Typically, carboxylic acids in the range of $C_2$ to $C_{18}$ are employed in this step. Direct esterification of epoxides is more fully detailed in commonly-assigned U.S. patent application Ser. No. 12/023,695; filed Jan. 31, 2008.

In the case of direct esterification of the epoxide (i.e., the esterification step), in some embodiments this step is carried out in the presence of a catalyst. Such catalyst species can include, but are not limited to, $H_3PO_4$, $H_2SO_4$, sulfonic acid, Lewis acids, silica and alumina-based solid acids, amberlyst, tungsten oxide, and mixtures and combinations thereof, and the like.

4.3 Esterification via a Diol Intermediate

Figure 4:
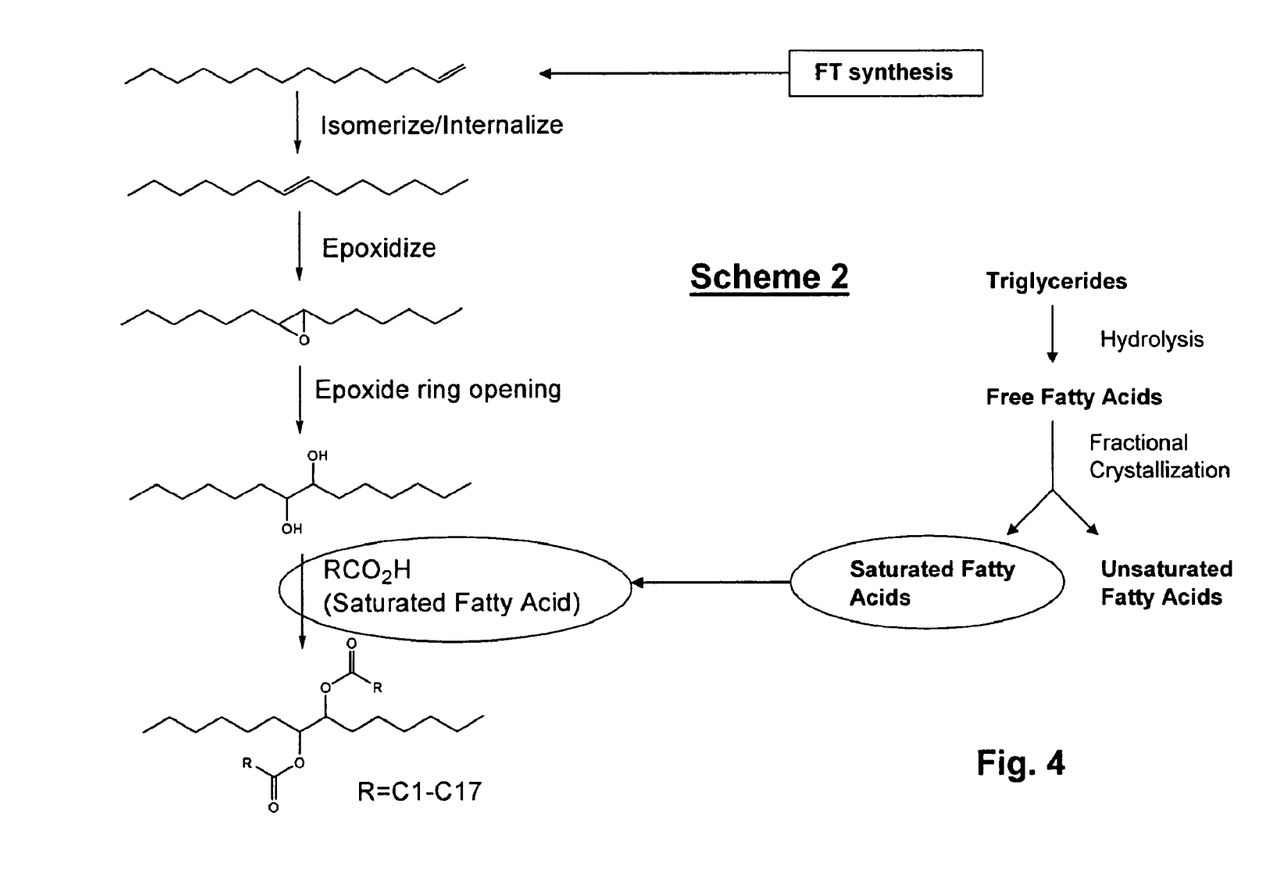
FIG. 4 (Scheme 2) is a chemical flow diagram illustrating an exemplary method of making a diester-based lubricant composition whereby the synthesis proceeds through a diol species, in accordance with some embodiments of the present invention.

In some embodiments, the step of esterifying proceeds through a diol intermediate—as shown in FIG. 4, Scheme 2. Typically, carboxylic acids in the range of $C_2$ to $C_{18}$ are used in this step. Details of such esterification can be found in commonly-assigned U.S. patent application Ser. No. 11/673,879; filed Feb. 12, 2007.

Regarding the step of epoxide ring opening to the corresponding diol, this step can be acid-catalyzed or based-catalyzed hydrolysis. Exemplary acid catalysts include, but are not limited to, mineral-based Brönsted acids (e.g., HCl, $H_2SO_4$, $H_3PO_4$, perhalogenates, etc.), Lewis acids (e.g., $TiCl_4$ and $AlCl_3$) solid acids such as acidic aluminas and silicas or their mixtures, and the like. See, e.g., Chem. Rev. vol. 59, p. 737, 1959; and Angew. Chem. Int. Ed., vol. 31, p. 1179, 1992. Based-catalyzed hydrolysis typically involves the use of bases such as aqueous solutions of sodium or potassium hydroxide.

Regarding the step of esterifying (esterification), an acid is typically used to catalyze the reaction between the —OH groups of the diol and the carboxylic acid(s). Suitable acids include, but are not limited to, sulfuric acid (Munch-Peterson, Org. Synth., V, p. 762, 1973), sulfonic acid (Allen and Sprangler, Org Synth., III, p. 203, 1955), hydrochloric acid (Eliel et al., Org Synth., IV, p. 169, 1963), and phosphoric acid (among others). In some embodiments, the carboxylic acid used in this step is first converted to an acyl chloride (via, e.g., thionyl chloride or PCl$_3$). Alternatively, an acyl chloride could be employed directly. When an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. See, e.g., Fersh et al., J. Am. Chem. Soc., vol. 92, pp. 5432-5442, 1970; and Hofle et al., Angew. Chem. Int. Ed. Engl., vol. 17, p. 569, 1978.

4.4 Carboxylic Acid Generation

Generally, at least some of the carboxylic acids used in the above-described methods are derived from biomass. In some such embodiments, this involves the extraction of some oil (e.g., triglyceride) component from a triglyceride-bearing biomass source such as algae. In such embodiments, the triglycerides must typically be hydrolyzed to form free acids. In some such embodiments, the hydrolyzing involves an acid hydrolysis. See, e.g., Bondioli, "The preparation of fatty acid esters by means of catalytic reactions," Topics in Catalysis, vol. 27 (1-4), pp. 77-82, 2004.

In some embodiments, carboxylic acids are additionally derived from other non-biomass sources (e.g., Fischer-Tropsch synthesis). Such alternatively-derived carboxylic acids could be mixed with the biomass-derived carboxylic acid prior to the step of esterifying. Such mixing could serve to alleviate logistical and/or supply related issues involving biomass.

In some embodiments, the quantity of carboxylic acids can comprise $C_2$ to $C_{18}$ carboxylic acids. Those of skill in the art will recognize that the types and lengths of the carboxylic acids are dependent upon the biomass source from which they are derived.

In some embodiments, the separation technique used to substantially isolate the saturated fatty acids involves fractional crystallization. See, e.g., Newey et al., "Drying Oils and Resins: Segregation of Fatty Acids and Their Derivatives by Extractive Crystallization with Urea," Industrial & Engineering Chemistry, vol. 42 (12), pp. 2538-2541, 1950. In some embodiments, other separation techniques known to those of skill in the art may additionally or alternatively be employed for selectively-isolating the saturated fatty acids.

4.5 Produced Ester Species

Generally, the ester species produced by the methods of the present invention are of the type described in Section 3. above.

In some embodiments, where a quantity of diester species is formed, the quantity of diester species can be substantially homogeneous, or it can be a mixture of two or more different such diester species. In the case of a mixture, such mixtures may also comprise relatively minor quantities of alcohols, monoesters, hydroxyl esters, and the like. Those of skill in the art will recognize that variety in the ester species produced can be largely attributed to variety in the precursor material and/or byproduct-producing side reactions made more favorable by certain reaction conditions.

5. Systems For Making Ester-Based Lubricants

As mentioned above, in some embodiments the present invention is directed to systems for implementing the methods of the present invention.

Figure 5:
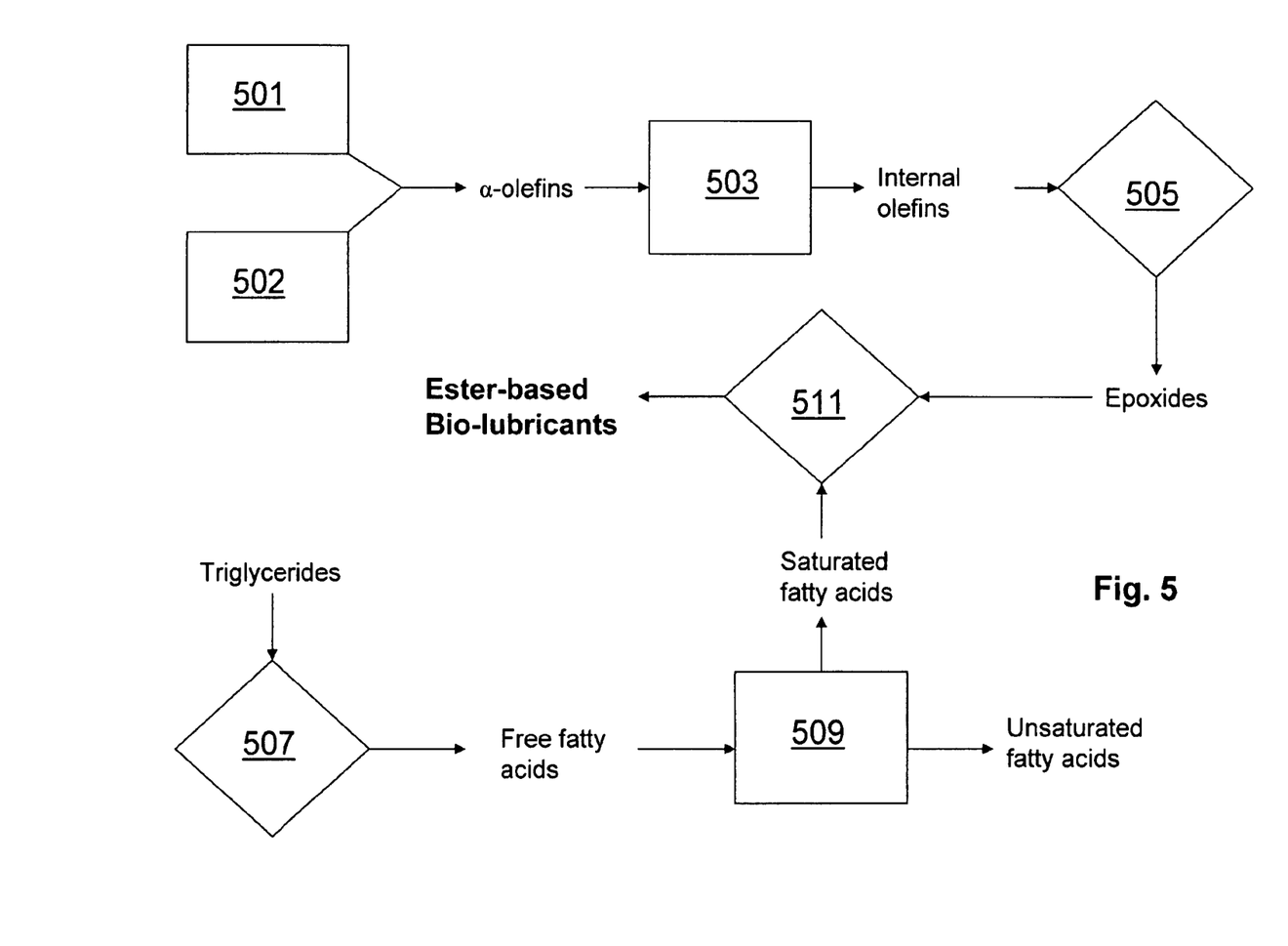
FIG. 5 depicts a system for implementing one or more of the method embodiments of the present invention.

Referring to FIG. 5, in some embodiments, the present invention is directed to one or more systems for producing ester-based biolubricants, such a system comprising: one or more reactor units for generating and subsequently isolating α-olefins via a technique such as Fischer-Tropsch processing of syngas (501) and/or pyrolysis of long-chain paraffinic species (502); an isomerization unit (503) for catalytically-isomerizing the α-olefins to form internal olefins; an epoxidation reactor (505) for converting at least some of the internal olefins to epoxides; and an esterification unit (511) for esterifying the epoxides with carboxylic acids to form ester species, wherein the carboxylic acids are derived from vegetable oil via a subsystem comprising: a hydrolysis unit (507) for hydrolyzing the triglyceride-bearing vegetable oil so as to generate a mixture of free fatty acids of varying degrees of saturation; and a separation unit (509) for separating the mixture of free fatty acids so as to substantially isolate saturated fatty acids contained therein for use in esterifying the aforementioned epoxides.

Olefin production from Fischer-Tropsch synthesis and/or pyrolysis of long-chain paraffinic species generally involve system component reactors suitably enabled to effect such olefin production, and they are typically further capable of being integrated with the overall system (i.e., system integration). Olefin production from pyrolysis of long-chain paraffinic species can involve pyrolysis of waste plastic, e.g., plastic containing polyethylene (PE).

In some embodiments, the esterification unit permits the esterification of the epoxides to proceed through diol intermediates. Additionally or alternatively, in these or other embodiments, the esterification unit permits the esterification of the epoxides to proceed directly, i.e., directly via esterification of the epoxide, as described above in Section 4.2.

In some embodiments, the separation unit utilizes fractional crystallization, as described above in Section 4.4. In some embodiments, other separation techniques may additionally or alternatively be employed in the system subcomponents for selectively-isolating the saturated fatty acids.

In some embodiments, the one or more reactor units additionally generate transportation fuel. Such reactor units can generate such fuel from any or all of the following sources: FT synthesis, pyrolysis of long-chain paraffinic species, and biomass.

6. Variations

As intimated above, variations (i.e., alternate embodiments) on the above-described embodiments include, but are not limited to, utilizing mixtures of isomeric olefins and or mixtures of olefins having a different number of carbons. This leads to diester mixtures in the product compositions. Additionally, in some embodiments, at least some of the α-olefins are not isomerized, and/or they are isomerized to different degrees. Additionally or alternatively, any of such olefin variations can be introduced directly (i.e., after the step of isomerizing), so as to allow more flexibility and control of the resulting product and/or to make the process/system more tolerant of variability in source/precursor streams. Still additionally (or alternatively), analogous carboxylic acid substitutions/variations can be introduced during or after the step of esterifying.

7. Examples

The following examples are provided to demonstrate, and/or more fully illustrate, particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Example 1

This Example serves to illustrate the direct esterification of 1-dodecene epoxide (2-decyl-oxirane) to yield a diester species, in accordance with some embodiments of the present invention.

Figure 6:
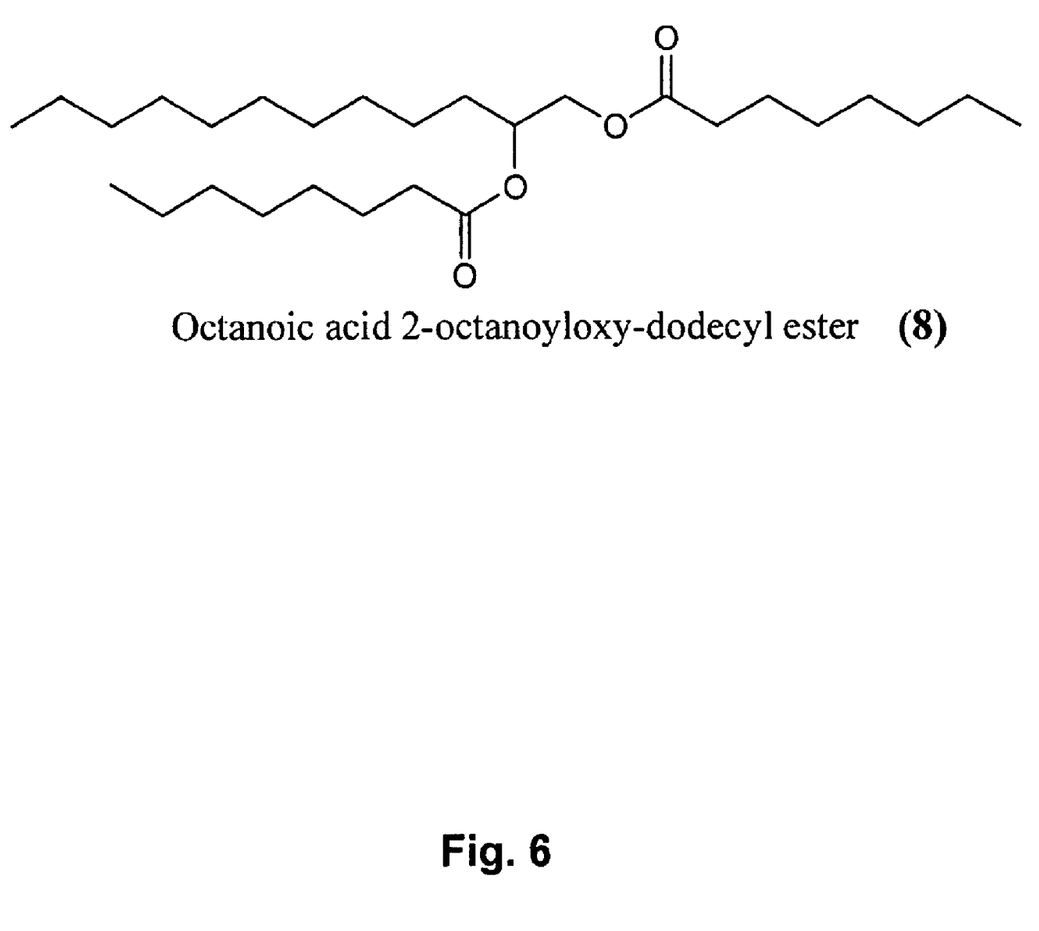
FIG. 6 depicts diester compound 8 made via direct esterification of an epoxide, in accordance with some embodiments of the present invention.

Quantities of 1-dodecene epoxide (9.2 grams, 50 mmol) and octanoic acid (14.4 grams, 100 mmol) were dissolved in 12 mL toluene, and 85% $H_3PO_4$ (0.3 grams, 0.87 mmol) was added. The mixture was stirred and bubbled/purged with nitrogen at 140° C. for 23 hours. The mixture was subsequently washed with a $K_2CO_3$-saturated solution, filtered and separated to remove the acids, the organic layer was dried by anhydrous $MgSO_4$ and evaporated under reduced pressure. Referring to FIG. 6, the diester product 8, octanoic acid 2-octanoyloxy-dodecyl ester, (18 grams, 83% yield) was a transparent, colorless oil.

Example 2

Figure 7:
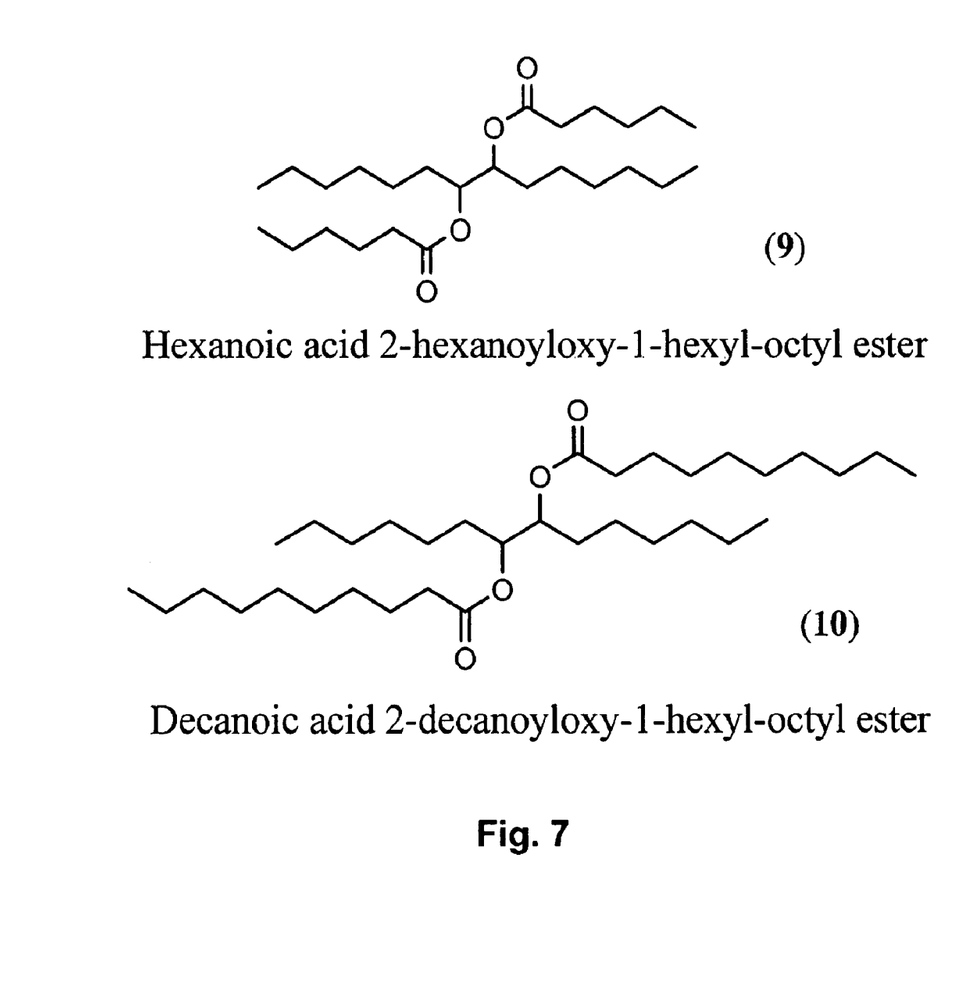
FIG. 7 depicts diester compounds 9 and 10, synthesized via a diol intermediate, in accordance with some embodiments of the present invention.

This Example serves to illustrate synthesis and isolation of a diol, and subsequent esterification of said diol, en route to synthesis of a diester species, in accordance with some embodiments of the present invention.
Diol Preparation and Isolation In a 3-neck 1 mL reaction flask equipped with an overhead stirrer and an ice bath, 75 mL of 30% hydrogen peroxide were added to 300 mL of 96% formic acid. To this mixture, 100 grams (0.51 mole) of 7-tetradecene (purchased from Aldrich Chemical Co.) was added slowly over a 30 minute period via a dropping funnel. Once the addition of the olefin was complete, the reaction was allowed to stir while cooling with the ice-bath to prevent rise in the temperature above 40-50° C. for 2 hrs. The ice-bath was then removed and the reaction was stirred at room temperature overnight. The reaction mixture was concentrated with a rotary evaporator in a hot water bath at ~30 torr to remove most of the water and formic acid. Then, 100 mL of ice-cold 1 M solution of sodium hydroxide was added very slowly (in small portions) and carefully to the remaining residue of the reaction. Once all the sodium hydroxide solution was added, the mixture was allowed to stir for an additional 45-60 minutes at room temperature. The mixture was diluted with 500 mL ethyl acetate and transferred to a separatory funnel. The organic layer was sequestered and the aqueous layer was extracted 3 times (3×200 mL) with ethyl acetate. The ethyl acetate extracts were combined and dried over anhydrous $MgSO_4$. Filtration, followed by concentration on a rotary evaporator at reduced pressure in a hot water bath gave the desired diol as white powder in 88% yield (95 grams). The produced and isolated diol (tetradecane-7,8-diol) was characterized by nuclear magnetic resonance (NMR) spectroscopy and gas-chromatography/mass spectrometry (GC/MS).
Conversion of the Diol to a Diester What follows serves to illustrate synthesis of diester 10 (decanoic acid 2-decanoyloxy-1-hexyl-octyl ester) from tetradecane-7,8-diol (see above). FIG. 7 depicts diester 10, as well as diester 9 (hexanoic acid 2-hexanoyloxy-1-hexyl-octyl ester), the latter being similarly prepared by using hexanoic acid or an anhydrous variant thereof.

In a 3-neck 1 L reaction flask equipped with an overhead stirrer, reflux condenser and a dropping funnel, 50 grams (0.23 mol) of tetradecane-7,8-diol (prepared above) and 60 grams (0.59 mol) triethylamine and a catalytic amount of dimethylaminopyridine (6.5 grams; 0.052 mol)) were mixed in 500 mL anhydrous hexane. The solution was cooled down with an ice bath. To this solution 97 grams (0.51 mol) decanoyl chloride was added drop-wise over a 15 minute period. Once the addition was complete, the ice bath was removed and the reaction was allowed to stir overnight. Then, an additional 12 grams of the decanoyl chloride was added and the reaction was refluxed overnight. The resulting "milky" reaction solution was neutralized with water. The resulting two layer mixture was then transferred to a separatory funnel. The organic (top) layer was separated and washed with 2×500 mL water. The aqueous layer was extracted with 3×300 mL ether. The ether extracts and the original organic layer were combined, dried over $MgSO_4$, filtered, and concentrated over a rotary evaporator at reduced pressure. The resulting residue was analyzed by NMR and infrared (IR) spectroscopies and GC/MS. Such analysis confirmed the presence of decanoic acid. The mixture was treated with 3 M aqueous solution of sodium carbonate (to neutralize the acid impurity) in 500 mL hexane. The hexane layer was dried over $MgSO_4$, filtered and concentrated on a rotary evaporator to give the desired diester product as a colorless viscous oil with a sweet odor in 81% yield (100.5 grams). CC/MS indicated the presence of less than 1% residual acid in the product.

8. Summary

In summary, the present invention is generally directed to the synthesis and/or manufacture of ester-based lubricant compositions, particularly those comprising one or more diester species. The present invention is also directed to methods of making these and other similar lubricant compositions, and to systems for implementing such methods. In some embodiments, the methods for making such ester-based lubricants utilize a biomass precursor, wherein at least an ester component of said lubricant is derived from a biomass source. In these or other embodiments, lubricant precursor species can also be sourced or derived from Fischer-Tropsch and/or pyrolysis of long-chain paraffinic species reaction products. The ester component of the lubricant compositions, produced in accordance with the methods and systems of the present invention, comprises largely diester species.

All patents and publications referenced herein are hereby incorporated by reference to an extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:
1. A method comprising the steps of:
    a) generating and subsequently isolating α-olefins from a process selected from the group consisting of Fischer-

Tropsch processing of syngas, pyrolysis of long-chain paraffinic species, and combinations thereof;

b) isomerizing the α-olefins to form internal olefins;

c) epoxidizing the internal olefins to form epoxides having an epoxide ring;

d) hydrolyzing a triglyceride-bearing vegetable oil so as to generate a mixture of free fatty acids of varying degrees of saturation;

e) subjecting the mixture of free fatty acids to a separation technique to substantially isolate saturated fatty acids; and f) esterifying the epoxides with at least a portion of the quantity of the saturated fatty acids to form ester species.

2. The method of claim 1, wherein the step of esterifying proceeds through a diol intermediate.

3. The method of claim 1, wherein the α-olefins are $C_2$ to $C_{20}$ olefins.

4. The method of claim 1, wherein the step of isomerizing the α-olefins is carried out via a catalytic process.

5. The method of claim 1, wherein the ester species so produced are selected from the group consisting of monoesters, diesters, and combinations thereof.

6. The method of claim 1, wherein the ester species are operable for use as lubricants.

7. The method of claim 1, wherein the process of generating α-olefins additionally produces transportation fuel.

8. The method of claim 1, wherein the quantity of saturated fatty acids can comprise $C_2$ to $C_{18}$ carboxylic acids.

9. The method of claim 1, wherein the separation technique used to substantially isolate the saturated fatty acids involves fractional crystallization.

10. The method of claim 1, wherein the step of hydrolyzing comprises an acid hydrolysis.

* * * * *